Figure 1:
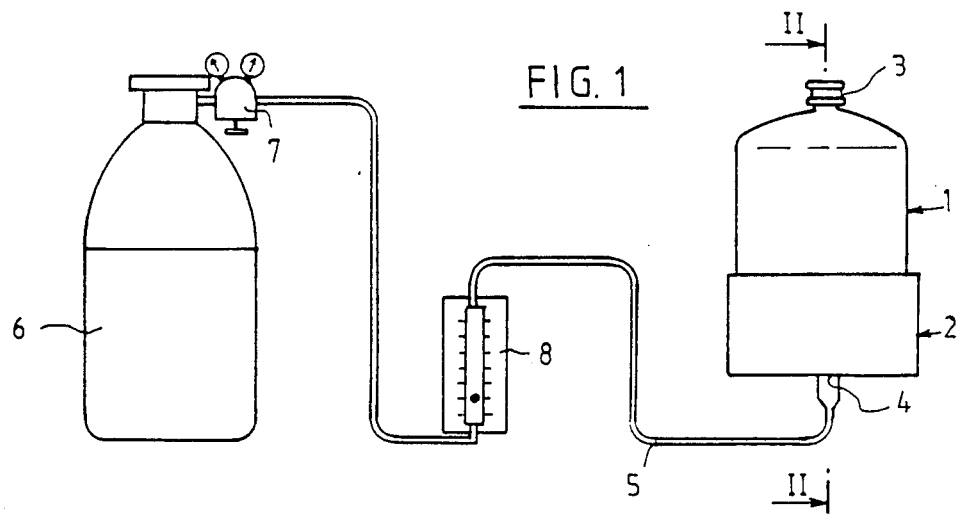

United States Patent [19]

Vigneau et al.

[11] Patent Number: 4,693,235
[45] Date of Patent: Sep. 15, 1987

[54] GAS HEATING PROCESS AND APPARATUS

[75] Inventors: Jean L. Vigneau, Varilhes; Pierre Trenque, Ramonville St Agne, both of France

[73] Assignee: Duffour et Igon S.A. (D.I.), Toulouse, France

[21] Appl. No.: 800,381

[22] Filed: Nov. 21, 1985

[30] Foreign Application Priority Data

Nov. 23, 1984 [FR] France .................................. 84 17850

[51] Int. Cl.⁴ ................................................. F24J 1/00
[52] U.S. Cl. ................................. 126/263; 128/204.17
[58] Field of Search ............................... 126/263, 204; 128/204.17

[56] References Cited

U.S. PATENT DOCUMENTS 2,325,049  7/1943  Frye et al. ................. 128/204.17
3,923,059  12/1975 Chalon et al. ................... 126/263
4,501,259  2/1985  Apellaniz .................... 126/263

FOREIGN PATENT DOCUMENTS 1540375  2/1979  United Kingdom ........... 128/204.17

Primary Examiner—James C. Yeung
Attorney, Agent, or Firm—Birch, Stewart, Kolasch & Birch

[57] ABSTRACT

A gas heating process is disclosed in which a gas to be heated and carbonic gas causing an exothermic reaction with soda-lime are caused to pass simultaneously over a charge of soda-lime. The device of the invention includes a cartridge with a first chamber containing the charge of soda-lime and a second chamber containing the amount of carbonic gas required for starting the exothermic reaction, and a means for placing the two chambers in communication. The first chamber is connected to an inlet for the mixture of gas to be heated and carbonic gas for maintaining the reaction, and also is connected to an outlet (3) for the heated gas.

18 Claims, 2 Drawing Figures

GAS HEATING PROCESS AND APPARATUS

The present invention relates to a gas heating process in which there is caused to pass simultaneously, over a charge of soda-lime, the gas to be heated and carbonic gas causing an exothermic reaction with the soda-lime. The present invention also relates to a device for implementing this process.

Heating a gas which is initially cold or at ambient temperature occurs extensively in the medical field. In this particular application, air or oxygen is heated which a patient then inhales so as to provide him with additional heat. Thus, hypothermia can be efficiently combatted, whether it is accidental, as in the case of victims injured in road accidents, lost in the mountains or drowned, or whether it is caused by a long surgical operation or an extended exposure at low temperatures.

For this procedure, the exothermic reaction of soda-lime in the presence of carbonic gas has already been. This procedure has the advantage of making the production of heat independent of an external source of energy.

This reaction, whose formula is the following:
$$2CaO + 2NaOH + 3CO_2 \rightarrow 2CaCO_3 + N_2CO_3 + H_2O + \text{heat},$$
is very well known and it is already used in the medical field for purifying the gases exhale by patients during anaesthesia.

However, any practical application to the heating of gases has not been successful up to now because of the difficulty in maintaining the reaction. In fact, the temperature at the beginning of the reaction may rise above the threshold admissible for the patient. In addition, since the carbonic gas saturates the soda-lime, when the saturation threshold is exceeded, there is a risk of the patient breathing in an unacceptable concentration of carbonic gas. Finally, the massive production of heat at the beginning of the reaction causes an overconsumption which is prejudicial to the self sufficiency of the system.

The main aim of the present invention is to overcome these drawbacks and, accordingly, the present invention provides a process of the above mentioned type which is essentially characterized in that it consists in placing the soda-lime in the presence of a predetermined amount of carbonic gas so as to rapidly initiate the exothermic reaction and in causing a mixture of gas to be heated and carbonic gas in given proportions to pass over the soda-lime so as to maintain the exothermic reaction.

Thus the reaction may be well controlled, which allows more powerful, rapid and stable heating to be obtained over a relatively long period of time. In addition, the heating temperature may be readily adjusted by simply varying the proportion of the mixture of gases to be heated and carbonic gas.

The device for implementing the process of the invention comprises a cartridge with a first chamber containing the charge of soda-lime and a second chamber containing the amount of carbonic gas required for initiating the exothermic reaction, and a means for placing the two chambers in communication. The first chamber is connected on the one hand to an inlet for the mixture of gases to be heated and carbonic gas for maintaining the reaction and, on the other hand, to an outlet for the heated gas.

Preferably, the device also comprises a heater body on which the cartridge can be removably fixed. The positioning of the cartridge on the heater body automatically causes the two chambers to be placed in communication.

Thus an extremely practical assembly is provided which may be used very rapidly in the case of emergencies.

In another particular embodiment of the invention, the first chamber is formed at the center of the cartridge, whereas the second chamber is formed by a hermetic annular chamber surrounding the first chamber. The said first central chanber opens at its upper part into a decantation chamber connected to the heated gas outlet and at its lower part into an intake chamber formed between the bottom of the cartridge and the base of the heater body in which is disposed the inlet for the mixture of gas to be heated and carbonic gas maintaining the reaction.

Furthermore, the first central chamber is advantageously separated from the intake chamber by a grid providing a uniform distribution of the gas flow over the soda-lime and from the decantation chamber by a dust filter.

Preferably, the means for automatically causing the two chambers to be placed in communication is formed by a striker placed on the heater body and adapted for perforating a membrane hermetically sealing the second chamber during positioning of the cartridge on the heater body, the carbonic initiating gas then flowing towards the first chamber through the intake chamber.

Figure 2:
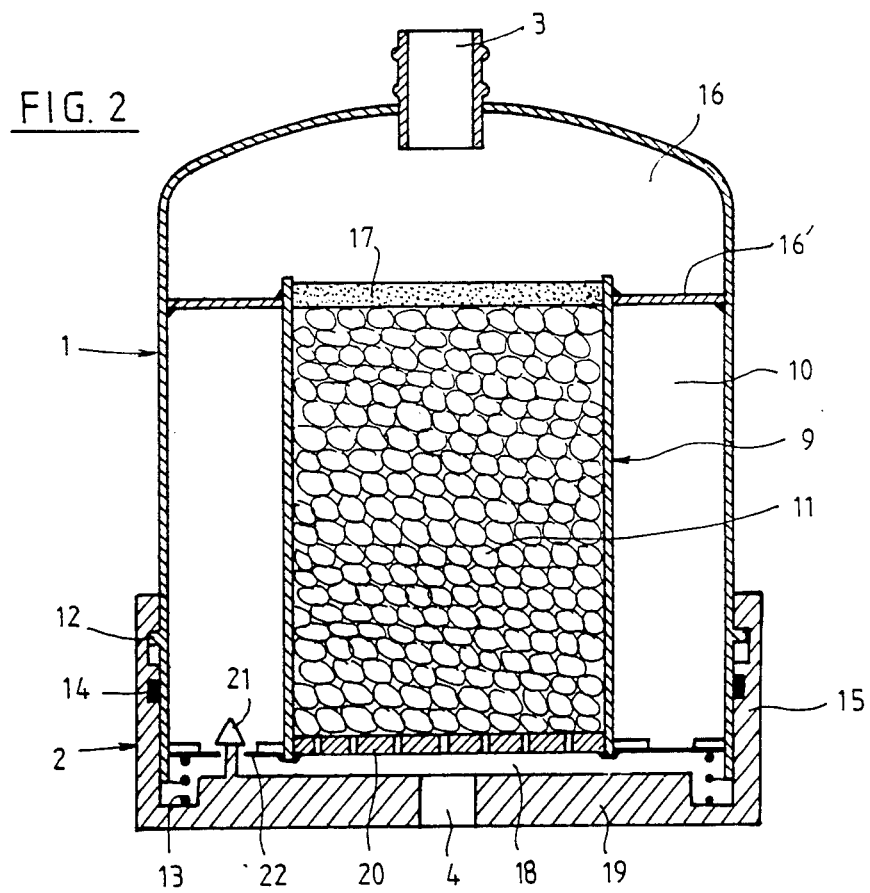

One embodiment of the invention is described hereafter by way of example, with reference to the accompanying drawings, and wherein FIG. 1 is a schematic view of the gas heating device in accordance with the present invention, and FIG. 2 is an enlarged cross-sectional view along line II—II of FIG. 1.

The device shown in FIG. 1 comprises first of all a cartridge 1 which is removably fixed to a heater body 2. Cartridge 1 is covered by an end piece 3 forming an outlet for the heated gas, whereas the heater body 2 comprises at its lower part an inlet 4 which is connected by a pipe 5 to a cylinder 6 containing a compressed mixture of cold gas to be heated and carbonic gas. A pressure reducer-regulator 7 is disposed at the outlet of cylinder 6 and a constant flow generator 8 is in addition inserted in pipe 5, so that the gas mixture arrives at the heater body 2 with suitable flow and pressure.

As can be seen in FIG. 2, cartridge 1 is essentially formed by an enclosure of cylindrical shape inside which are formed a first central chamber 9 and a second annular chamber 10 surrounding the first one. The central chamber 9 contains a predetermined amount of soda-lime 11 whereas the annular chamber 10 contains a predetermined amount of carbonic gas required for initiating the exothermic reaction with the soda-lime 11.

Cartridge 1 is removably fixed to the heater body 2 by appropriate means, for example by screwing or, as shown at 12, by a bayonet system operating in association with a compensation spring 13 which is housed in the heater body. An O seal 14 is further provided on the cylindrical part 5 of the heater body 2 for providing a sealed connection with the cartridge.

The central chamber 9 with the soda-lime 11 opens at its upper part into a decantation chamber 16 connected to the heated gas outlet 3 and which is intended to collect the water which condenses at the top of the cartridge. If required, a condenser may be provided for applications where the amount of water generated by the reaction is undesirable.

A dust filter 17 is further inserted between the soda-lime 11 and a decantation chamber 16.

It will be further noted that the wall forming the central chamber 9 extends inside the decantation chamber 16, thus forming an annular retention zone 16' in which the condensation water accumulates. It is in fact important that this water does not come into contact with the soda-lime 11. If necessary, an absorbent material may be disposed in the annular zone 16', so that the cartridge may be used in a more or less slanted position.

In its upper part, the central chamber 9 opens into an intake chamber 18 formed between the bottom of cartridge 1 and the base 19 of the heater body 2, into which intake chamber also opens the inlet 4 for the mixture of gas to be heated and carbonic gas. A grid 20 is further inserted between the central chamber 9 and the intake chamber 18 for providing a uniform distribution of the gas flow over the mass of lime conatining soda 11.

On the base 19 of the heater body 2, is also disposed laterally a striker 21 adapted to automatically perforate, during positioning of the cartridge 1, a membrane 22 for example made from a metal foil, normally hermetically sealing the annular chamber 10 in which is held the carbonic gas required for starting the reaction.

Cartridge 1 is normally designed for a single one-time use. In fact, since the carbonic gas required for starting the reaction will have been completely freed during the first use by action of striker 21, the cartridge cannot be reused, even if it has only been used partially.

The cartridge may be designed either to be thrown away after use or to be reconditioned industrially. In this latter case, means will have to be provided for replacing the charge of soda-lime 11 and filling the annular chamber 10 with a new amount of starting carbonic gas.

To prevent the soda-lime 11 from being impaired, cartridge 11 will be sealed at its inlet, i.e. at the level of grid 20 and at its outlet 3, by a cap or a sealing film which will have to be ripped off when it is brought into service. This arrangement also allows a new cartridge to be readily distinguished from a old cartridge.

After connecting the outlet 3 to the user circuit, formed for example by a breathing apparatus, cartridge 1 is fitted into the heater 2 by means of the bayonet system 12 and it is locked in position. Meanwhile, striker 21 perforates the foil 22 forming a calibrated orifice through which the carbonic starting gas escapes which is contained inside the annular chamber 10. Since sealing is provided at the level of seal 14, this carbonic gas spreads first of all into the intake chamber 18 and then penetrates into the central chamber 9 containing the charge of soda-lime, through the flow dividing grid 20.

The exothermic reaction is immediately started. The temperature rises in a few seconds and reaches the required level in about 2 to 3 minutes.

It then only remains to inject in the inlet 4 the cold gas to be heated and the carbonic gas required for maintaining the exothermic reaction. In the particular embodiment shown, the carbonic reaction-maintaining gas is previously diluted in the cold gas, thus forming a predetermined mixture. Thus a single source is obtained, formed by cylinder 6, which is particularly convenient in emergency cases, for example, for treating victims of accidents and provides a very compact construction facilitating transport.

Of course separate cold gas and carbon gas supplies could be provided, and the mixture formed on the spot, either directly at the level of the intake chamber 18 with two separate intakes for the two gases, or upstream with only a single input in the heater body.

Furthermore, the carbonic starting gas and the mixture of cold gas and carbonic maintaining gas may be injected into the cartridge successively, or else simultaneously, without substantially modifying the characteristics. Thus, in particular the inlet 4 could be supplied with the mixture of cold gas and carbonic maintaining gas before placing the cartridge 1 in position on the heater body 2.

For safety reasons, the total mass of carbonic starting gas and carbonic maintaining gas must be less than the saturation mass of the charge of soda-lime.

By way of example, with a mass of soda lime of 0.7 kg, a standard cylinder of a capacity of 5 liters of water could be used, capable of containing 1 $m^3$ of gas compressed at $200.10^5$ Pa, with a concentration of 7.5% carbonic maintaining gas, the mass of carbonic starting gas then being about 25 g.

The pressure reducer-regulator 7 brings the storage pressure of the compressed gas down to a value compatible with use thereof, i.e. about 1000 to 3000 Pa, whereas the flow rate generator 8 calibrates the flow drawn off to a constant value depending on the desired heating temperature. Thus temperatures are obtained between 40° and 80° C. for flow rates of carbonic maintaining gas going from 0.5 to 1.5 l/min.

With separated cold gas and carbonic maintaining gas supplies, it is of course easier to vary the heating temperature, for the carbonic gas concentration can then be varied without substantially modifying the flow rate at the outlet.

Moreover, the heating device of the present invention could also be equipped with different complementary safety devices. Thus for example a temperature probe could be provided for measuring the temperature of the hot gas at the outlet of the cartridge 1. In this case, the probe would be placed as close as possible to the user means for taking into account in-line heat losses.

A small carbonic gas analyzer may also if required, be provided for ensuring that the hot gas leaving the cartridge does not contain any carbonic gas.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. A process for heating a gas, which comprises the steps of:
   placing soda-lime in a chamber containing a predetermined amount of carbonic gas;
   contacting said predetermined amount of carbonic gas with said soda lime so as to initiate an exothermic reaction therebetween;
   passing a gas to be heated and a second amount of carbonic gas continuously into said chamber and over said soda-lime so as to maintain said reaction and heat said gas to be heated by heat produced from said reaction; and
   withdrawing heated gas from said chamber.
2. The process according to claim 1, wherein said gas to be heated and said second amount of carbonic gas are in the form of a mixture which is passed into said chamber.

3. The process according to claim 1, wherein said gas to be heated and said second amount of carbonic gas are separately passed into said chamber.

4. The process according to claim 1, wherein said gas to be heated and said second amount of carbonic gas are simultaneously passed into said chamber and passed over said soda-lime.

5. The process according to claim 1, wherein said gas to be heated and said second amount of carbonic gas are successively passed into said chamber and passed over said soda-lime.

6. The process according to claim 1, wherein said heated gas being withdrawn contains no carbonic gases.

7. An apparatus for heating a gas, comprising:
means for storing an amount of a gas to be heated and a
first amount of carbonic gas; and
a cartridge, including:
  a first annular chamber,
  a second annular chamber surrounding said first annular chamber,
  soda-lime contained in said first annular chamber,
  a predetermined amount of carbonic gas contained in said second annular chamber,
  means for permitting communication between said first annular chamber and said second annular chamber so that said predetermined amount of carbonic gas can contact said soda-lime and initiate an exothermic reaction,
  an inlet, connected to said first annular chamber, for continually receiving said gas to be heated and said first amount of carbonic acid permitting said gas to be heated and said first amount of carbonic gas to pass over said soda lime so as to maintain said exothermic reaction and heat said gas to be heated, and
  an outlet, connected to said first annular chamber, for withdrawing heated gas.

8. The apparatus of claim 7, which further comprises a heater body upon which said cartridge is removably fixed, and wherein said fixing of said cartridge to said heater body automatically permits communication between said first and second annular chambers.

9. The apparatus of claim 8, wherein said first annular chamber is cocentric with said cartridge and said second annular chamber is formed as a hermetic chamber surrounding said first annular chamber.

10. The apparatus of claim 9, wherein one end of said first annular chamber opens with a decantation chamber connected to said outlet for withdrawing heated gas.

11. The apparatus of claim 10, wherein the other end of said first annular chamber is connected to an intake chamber formed between a bottom of said cartridge and said heater body.

12. The apparatus of claim 11, wherein said heater body is provided with an inlet for receiving said gas to be heated and said first amount of carbonic gas and permitting both to enter said outlet of said cartridge.

13. The apparatus of claim 12, wherein said first chamber is separated from said intake chamber by a grid for ensuring a uniform distribution of gas over said soda-lime.

14. The apparatus of claim 10, wherein said first annular chamber is separated from said decantation chamber by a dust filter.

15. The apparatus of claim 8, wherein a means is provided for permitting said fixing of said cartridge to said heater body automatically to communicate between said first and second annular chambers, said means including:
  a membrane for hermetically sealing said second annular chamber; and
  a striker on said heater body for perforating said membrane so as to permit the flow of said predetermined amount of carbonic gas into said first annular chamber.

16. The apparatus of claim 7, wherein said means for storing is a container connected to said cartridge.

17. The apparatus of claim 6, wherein a gas line connects said container and said cartridge.

18. The apparatus of claim 16, wherein separate containers store said gas to be heated and said first amount of carbonic gas.

* * * * *